United States Patent
Bey et al.

(10) Patent No.: US 11,529,607 B2
(45) Date of Patent: Dec. 20, 2022

(54) REACTOR FOR CARRYING OUT A REACTION BETWEEN TWO NON-MISCIBLE FLUIDS OF DIFFERENT DENSITIES

(71) Applicant: BASF SE, Ludwigshafen am Rhein (DE)

(72) Inventors: Oliver Bey, Ludwigshafen am Rhein (DE); Peter Zehner, Weisenheim am Berg (DE); Mathias Schelwies, Ludwigshafen am Rhein (DE); Rocco Paciello, Ludwigshafen am Rhein (DE); Martin Haubner, Ludwigshafen am Rhein (DE); Guenter Wegner, Ludwigshafen am Rhein (DE); Gerd Tebben, Ludwigshafen am Rhein (DE); Gunnar Heydrich, Ludwigshafen am Rhein (DE); Georg Seeber, Ludwigshafen am Rhein (DE); Michael Acker, Ludwigshafen am Rhein (DE)

(73) Assignee: BASF SE, Ludwigshafen am Rhein (DE)

(\*) Notice: Subject to any disclaimer, the term of this patent is extended or adjusted under 35 U.S.C. 154(b) by 104 days.

(21) Appl. No.: 17/274,148

(22) PCT Filed: Sep. 3, 2019

(86) PCT No.: PCT/EP2019/073472
§ 371 (c)(1),
(2) Date: Mar. 5, 2021

(87) PCT Pub. No.: WO2020/048986
PCT Pub. Date: Mar. 12, 2020

(65) Prior Publication Data
US 2021/0275987 A1    Sep. 9, 2021

(30) Foreign Application Priority Data
Sep. 5, 2018   (EP) .................................. 18192755

(51) Int. Cl.
*B01J 19/26*    (2006.01)
*B01J 19/24*    (2006.01)
(Continued)

(52) U.S. Cl.
CPC ............. *B01J 19/26* (2013.01); *B01J 19/006* (2013.01); *B01J 19/244* (2013.01); *C07C 45/62* (2013.01);
(Continued)

(58) Field of Classification Search
CPC ........ B01J 19/26; B01J 19/006; B01J 19/244; B01J 2219/00768; B01J 2219/0884;
(Continued)

(56) References Cited

U.S. PATENT DOCUMENTS 4,000,212 A * 12/1976 Chapman .................. C07C 2/62
585/723

FOREIGN PATENT DOCUMENTS

WO    WO-2009153123 A1 * 12/2009 ............ B01J 19/246

\* cited by examiner

*Primary Examiner* — Huy Tram Nguyen
(74) *Attorney, Agent, or Firm* — Faegre Drinker Biddle & Reath LLP

(57) ABSTRACT

A reactor for performing a reaction between two immiscible fluids of different density, comprising an interior formed by a cylindrical, vertically oriented elongate shell, a bottom and a cap, wherein the interior is divided by internals into a backmixed zone, a zone of limited backmixing preferably arranged below the backmixed zone and a plug-flow zone which are at least consecutively traversable by one of the fluids, wherein the backmixed zone comprises at least one inlet and the plug-flow zone comprises an outlet and the backmixed zone comprises at least one mixing apparatus selected from a stirrer, a jet nozzle and means for injecting the fluid of lower density, a first cylindrical internal element which in the interior extends in the longitudinal direction of the reactor, which delimits the zone of limited backmixing from the plug-flow zone and which comprises a first passage to the backmixed zone and a second passage to the plug-flow zone, a second internal element which delimits the backmixed zone from the plug-flow zone such that there is no direct fluid connection between the backmixed zone and the plug-flow zone, and backmixing-preventing third internal elements in the form of random packings, structured packings or liquid-permeable trays arranged in the zone of limited backmixing. The reactor allows an optimal residence time distribution in the reaction of the two immiscible fluids (Continued)

of different density. The invention further relates to a process for performing a continuous reaction in the reactor.

20 Claims, 1 Drawing Sheet

(51) Int. Cl.
*B01J 19/00* (2006.01)
*C07C 45/62* (2006.01)

(52) U.S. Cl.
CPC ............... *B01J 2219/00768* (2013.01); *B01J 2219/0884* (2013.01); *B01J 2219/185* (2013.01); *B01J 2219/1943* (2013.01); *B01J 2219/2474* (2013.01); *B01J 2531/822* (2013.01)

(58) Field of Classification Search
CPC .......... B01J 2219/185; B01J 2219/1943; B01J 2219/2474; B01J 2531/822; B01J 31/24; B01J 31/2409; B01J 2219/00777; B01J 2219/0871; B01J 2231/643; B01J 3/042; B01J 10/00; B01J 19/2435; C07C 45/62; C07C 29/172; C07C 29/56; C07B 53/00
USPC ........................................................ 422/224
See application file for complete search history.

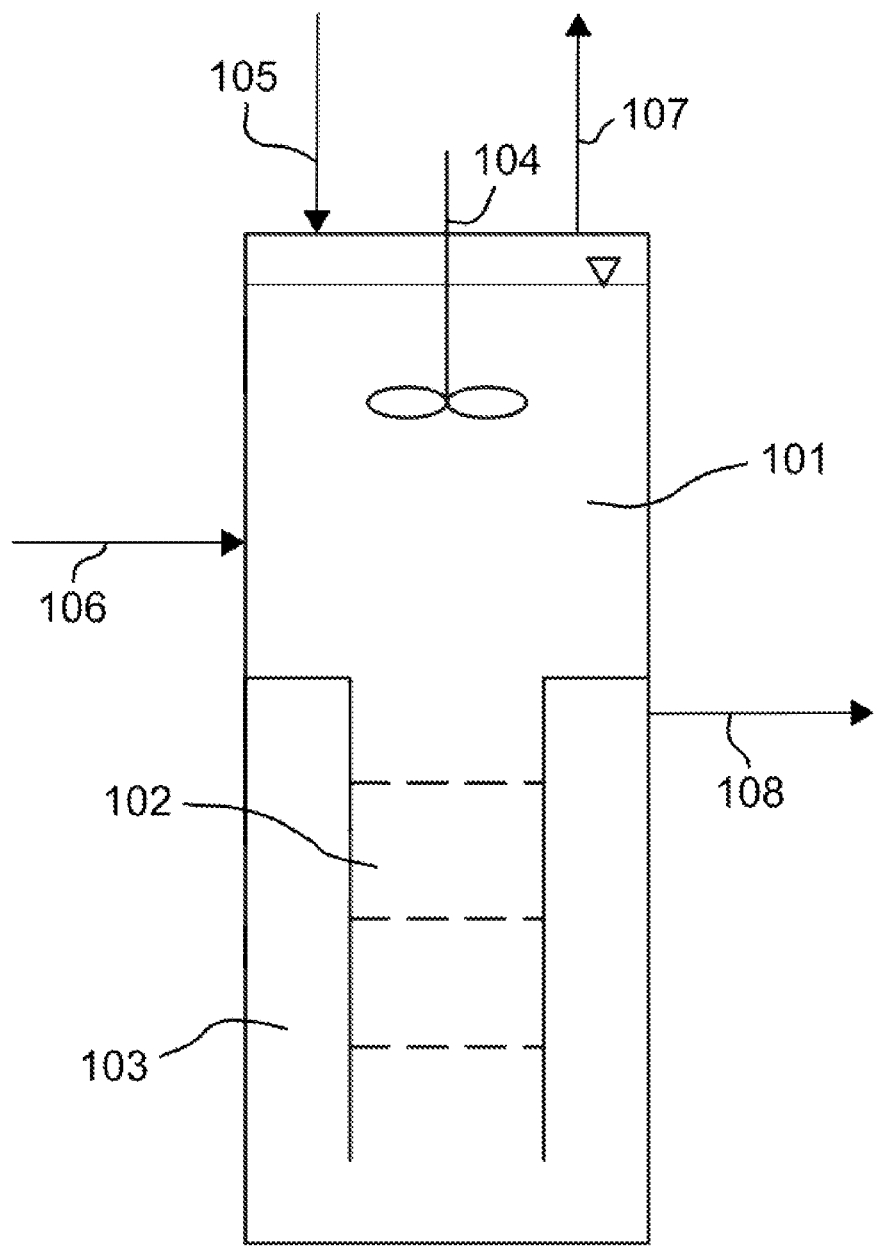

REACTOR FOR CARRYING OUT A REACTION BETWEEN TWO NON-MISCIBLE FLUIDS OF DIFFERENT DENSITIES

CROSS-REFERENCE TO RELATED APPLICATIONS

This application is a national stage application (under 35 U.S.C. § 371) of PCT/EP2019/073472, filed Sep. 3, 2019, which claims benefit of European Application No. 18192755.9, filed Sep. 5, 2018, both of which are incorporated herein by reference in their entirety.

The present invention relates to a reactor for performing a reaction between two immiscible fluids of different density and to a process for performing a continuous reaction in such a reactor.

Numerous conversions are performed by contacting immiscible fluids of different density. For example the hydrogenation of organic compounds makes use of the reaction of a dissolved hydrogenatable compound with gaseous hydrogen. It is known to perform the hydrogenation in a first backmixed zone and a second zone with limited backmixing. The backmixing in the first zone allows advantageous removal of reaction heat while the second zone is used for completion of reaction conversion.

WO 2009/153123 describes a continuous process for the hydrogenation of organic compounds in a multiphase system in the presence of a homogeneous or heterogeneous catalyst in which the process is performed in two stages, the first being performed in a loop reactor with external heat exchanger and the second stage in a bubble-column reactor with limited backmixing.

EP 1 338 333 A1 describes a reactor cascade composed of a sealed main reactor and a sealed postreactor, wherein the postreactor is located inside the main reactor vessel.

EP 1 231 198 A1 describes a continuous process for hydroformylation of olefins which employs a reactor comprising two consecutively traversable reaction spaces, wherein the second reaction space may comprise perforated plates.

Sufficient dispersing of the gaseous reaction partner hydrogen in the liquid reaction mixture is required for the reaction to proceed. However, the hydrogenation itself takes place in the liquid phase. The presence of hydrogen gas over and above the amount required for the hydrogenation conversion therefore reduces the reaction volume available for the hydrogenation. It is advantageous to optimally utilize the available reaction space.

Such a difficulty is in principle encountered in the reaction of mutually immiscible fluids of different density. It is the object of the invention to provide a reactor for performing a reaction between two immiscible fluids of different density which allows an optimal residence time distribution according to the requirements of the respective reaction.

The object is achieved by a reactor for performing a reaction between two immiscible fluids of different density, comprising an interior formed by a cylindrical, vertically oriented elongate shell, a bottom and a cap, wherein the interior is divided by internals into a backmixed zone, a zone of limited backmixing preferably arranged below the backmixed zone and a plug-flow zone which are at least consecutively traversable by one of the fluids, wherein the backmixed zone comprises at least one inlet and the plug-flow zone comprises an outlet and the backmixed zone comprises at least one mixing apparatus selected from a stirrer, a jet nozzle and means for injecting the fluid of lower density, a first cylindrical internal element which in the interior extends in the longitudinal direction of the reactor, which delimits the zone of limited backmixing from the plug-flow zone and which comprises a first passage to the backmixed zone and a second passage to the plug-flow zone, a second internal element which delimits the backmixed zone from the plug-flow zone such that there is no direct fluid connection between the backmixed zone and the plug-flow zone and backmixing-preventing third internal elements in the form of random packings, structured packings or liquid-permeable trays arranged in the zone of limited backmixing.

In a preferred embodiment the first internal element is arranged concentrically to the shell so that the plug-flow zone has an annular horizontal cross section.

In a preferred embodiment the lower edge of the first internal element is arranged at a distance from the bottom of the reactor and thus forms the passage from the zone of limited backmixing to the plug-flow zone.

In a preferred embodiment the second internal element extends from the upper edge of the first internal element to the shell. The second internal element is for example a horizontally oriented annular plate. The second internal element divides the interior in the vertical direction into an upper half and a lower half, for example in the ratio of the upper half to the lower half of 4:1 to 1:1, preferably in the ratio of 3:1 to 1:1, especially in the ratio of 2:1 to 1:1, for example 6:4.

The ratio of reactor length to reactor diameter is typically 2:1 to 100:1, preferably 5:1 to 50:1, more preferably 7:1 to 25:1.

Introduction of the fluids is carried out at any desired point of the backmixed zone. The backmixed zone comprises at least one mixing apparatus selected from a stirrer, a jet nozzle and means for injecting the fluid of lower density. This ensures that the two mutually immiscible fluids of different density are brought into intensive contact with one another.

Fluid of low density collects above the separation level of the fluids in the backmixed zone. In a preferred embodiment the unconverted fluid of lower density may be withdrawn from the backmixed zone via a fluid outlet.

In one embodiment the mixing apparatus is a stirrer, for example a propeller stirrer.

Alternatively, the introduction of the fluids may be carried out such that commixing of the backmixed zone is simultaneously accomplished. The fluid of high density (i.e. the liquid in gas/liquid reactions) is preferably introduced via a jet nozzle. The introduction via a jet nozzle may be carried out above or below the separation level of the fluids, in particular via a downwardly directed jet nozzle arranged above the separation level (liquid level).

The jet from the nozzle ensures dispersion of the fluids of low density in the reaction mixture. If for example the first fluid is a liquid and the second fluid is a gas the jet from the nozzle passes through the low density space and upon entry into the liquid phase impacts the gas which is thus broken up into bubbles and dispersed in the liquid phase.

The jet nozzle can be configured as a single-fluid or two-fluid nozzle. In the case of the single-fluid nozzle only one fluid is introduced. The advantage of this configuration is the simple construction of such a single-fluid nozzle. In the case of the two-fluid nozzle mutually immiscible fluids optionally having different densities are combined and dispersed.

In order to jointly introduce the fluid of low density (gas) together with the fluid of high density (liquid) the jet nozzle may be configured as a mixing nozzle, for example a multistream ejector mixing nozzle (liquid jet ejector). The term "mixing nozzle" typically refers to a tube that narrows in the flow direction. The ejected fast jet generates negative pressure in an aspiration space surrounding the nozzle. This allows fluid of low density to be aspirated and through impulse exchange dispersed in the fluid of high density and jointly therewith released into the backmixed zone.

In a further embodiment the mixing apparatus comprises means for injecting the fluid of lower density into the fluid of higher density. Suitable means for injecting the fluid of lower density are for example a compressor for aspirating and compressing the fluid of low density (in particular gas) above the separation level or of fresh fluid and nozzles for injecting the compressed fluid below the separation level.

The volume-specific power input into the backmixed zone is preferably 0.5 to 5 $kW/m^3$. The volume-specific power input can be determined as the product of the pressure differential across the jet nozzle and volume flow through the nozzle.

The backmixed zone is preferably configured as a loop reactor. Examples of loop reactors are tubular reactors having internal and external loops. Such reactors are described in more detail for example in Ullmann's Encyclopedia (Ullmann's Encyclopedia of Industrial Chemistry, Verlag Chemie, Electronic Release 2008, 7th edition, chapters "Stirred Tank and Loop Reactors" and "Bubble Columns").

The loop reactor is generally configured as a tubular reactor having an external circuit (external loops). A loop reactor having an external circuit generally has a takeoff at any desired point in the backmixed zone, preferably in the lower region of the backmixed zone, through which the reaction mixture is in an external circuit returned to the jet nozzle using a conveying apparatus. The conveying apparatus is preferably a pump and the external circuit is therefore typically referred to as a pumped circulation circuit.

Examples of pumps are centrifugal pumps or rotary piston pumps, such as rotary lobe pumps, rotary vane pumps, circumferential piston pumps or gear pumps. It is particularly preferable to employ centrifugal pumps as the conveying apparatus.

The backmixed zone is preferably configured as a loop reactor having an external circuit, wherein the external circuit comprises a heat exchanger. In the context of the present invention such a reactor is referred to as a loop reactor having an external heat exchanger.

The heat exchanger is for example a tube bundle heat exchanger, double tube heat exchanger, plate heat exchanger or spiral heat exchanger. At reactor design pressures below 100 bar it is preferable to use a tube bundle heat exchanger while at higher pressures it is preferable to use one or more double tube heat exchangers connected in series.

The loop reactor with external heat exchanger is typically operated such that a portion of the reaction mixture from the backmixed zone is conveyed through the external pumped circulation circuit comprising the external heat exchanger, thus cooling the reaction mixture conveyed through the heat exchanger. The external pumped circulation generally vigorously commixes and recirculates the reaction mixture in the first reaction stage so that the residence time in the first stage typically corresponds to that of a continually backmixed stirred tank (CSTR).

The reaction mixture is finally returned to the backmixed zone by means of the jet nozzle. Typically, fluid to be converted and optionally a catalyst solution are introduced into the pumped circulation circuit and together with the stream already present in the pumped circulation circuit supplied to the backmixed zone of the reactor as reaction mixture.

In a preferred embodiment the loop reactor is configured such that a so-called internal loop flow is formed in addition to the external circuit. A loop reactor having internal loop flow generally has arranged in it in the interior of the backmixed zone a concentric, preferably cylindrical guide tube which extends substantially over the entire length of the backmixed zone with the exception of the region of the cap and the region of the second internal element.

The guide tube is normally configured as a simple tube. The length-to-diameter ratio of the guide tube is generally 5:1 to 100:1, preferably 5:1 to 50:1.

The diameter of the guide tube is less than the diameter of the backmixed zone. The ratio of the diameter of the guide tube to the diameter of the backmixed zone is generally 0.3:1 to 0.9:1, preferably 0.5:1 to 0.7:1. The space between the guide tube and the shell is generally referred to as the annular gap.

The jet nozzle is typically arranged such that the fluid jet generated by the jet nozzle is directed into the guide tube. The jet nozzle is preferably arranged above the upper end of the guide tube. The nozzle tip of the jet nozzle for the fluid of higher density is located above the liquid level and is not immersed in the liquid phase. The fluid jet generated by means of the jet nozzle causes a downward flow in the guide tube (downflow column) which after exiting the guide tube is deflected such that the liquid in the annular gap between the guide tube and the shell flows upward toward the jet nozzle again (upflow column). This generally results in an internal loop flow. The ratio of volume flows of the internal loop flow to the reaction mixture in external pumped circulation is preferably 2 to 30:1, particularly preferably 5 to 20:1.

From the backmixed zone at least a portion of the reaction mixture is supplied to the zone of limited backmixing. In the zone of limited backmixing the residence time distribution approaches the residence time distribution of a tubular reactor. This defined liquid residence time makes it possible to elevate the conversion of the reactant.

Adjusting the volume ratio of the backmixed zone to the zone of limited backmixing makes it possible to adapt the residence time distribution according to the requirements of the reaction to be performed. The volume ratio of the backmixed zone to the zone of limited backmixing is preferably in the range from 9:1 to 6:4, in particular in the range from 8:2 to 6:4 and very particularly preferably in the range from 7:3 to 6:4, for example 7:3.

Backmixing in the reactor is limited by backmixing-preventing third internal elements arranged in the zone of limited backmixing. The installation of such elements generally limits the circulation and thus the backmixing of fluids of different density, for example gas and liquid.

The limiting of backmixing in the reactor may be realized through installation of various internals in the zone of limited backmixing. In a preferred embodiment the limiting of backmixing is effected through installation of a plurality of fixedly arranged trays in the first cylindrical internal element. This results in formation of individual segments ("compartments") having defined reaction volumes between the individual trays. Each of the individual segments generally acts as an individual, backmixed stirred-tank reactor. As the number of individual segments in series increases the residence time distribution of such a cascade generally approaches the residence time of a tubular reactor.

The number of the thus formed individual segments is preferably 2 to 20, particularly preferably 2 to 10, especially preferably 3 to 6. The trays are preferably in the form of liquid-permeable trays. It is particularly preferable when the trays are perforated plates.

In a further embodiment the limiting of backmixing is effected through installation of random packings. The random packings may have different shapes and are usually about 2 to 15 mm in size. Known examples include spherical and cylindrical solid bodies, raschig rings (a hollow cylinder), pall rings, hiflow rings, Intalox saddles and the like. The random packings are preferably solid bodies. The random packings may be introduced into the zone of limited backmixing in ordered or disordered form (as a dumped bed). Materials that may be employed include glass, ceramic, metal and plastics.

In a further embodiment the limiting of backmixing is effected through incorporation of structured packings. Structured packings are a further development of ordered random packings. They have a regular structure. There are various designs of packings, such as woven or sheet metal packings. Materials that may be employed include metal, plastic, glass and ceramic.

In the case of a gas/liquid biphasic reaction the reaction is advantageously effected in a section of the zone of limited backmixing toward the exit from the zone of limited backmixing in a single liquid phase, i.e. the section toward the exit from the zone of limited backmixing contains no dispersed gas phase and the reaction is effected exclusively with the gas dissolved in the liquid phase. A hydrogenation with hydrogen gas for example may be performed in the reactor.

Since the hydrogenation conversions toward the exit from the zone of limited backmixing are typically low the concentration of dissolved hydrogen is sufficient. The absence of a discrete gas phase toward the exit from the zone of limited backmixing makes it possible to increase the liquid holdup in the zone of limited backmixing and increase the residence time of the liquid phase in the zone of limited backmixing. Since the hydrogenation takes place in the liquid phase, this makes optimal use of the reaction space.

The section of the zone of limited backmixing operated with a single liquid phase preferably accounts for 30% to 50% of the total volume of the zone of limited backmixing.

From the zone of limited backmixing the reaction mixture finally passes into the plug-flow zone. Backmixing is limited in the plug-flow zone and so the residence time distribution in this zone further approximates that of a tubular reactor. This defined liquid residence time makes it possible to achieve virtually complete conversion of the reactant.

In the case of a gas/liquid biphasic reaction it is preferable when at least at the exit from the zone of limited backmixing, i.e. upon entry into the plug-flow zone, no dispersed gas phase is present and the reaction is effected exclusively with the gas dissolved in the liquid phase. Since the conversions in the plug-flow zone are typically low the concentration of dissolved gas is sufficient. The absence of a discrete gas phase in the plug-flow zone makes it possible to increase the liquid holdup and increase the residence time of the liquid phase in the plug-flow zone. The reaction space is thus optimally utilized.

The volume ratio of the zone of limited backmixing to the plug-flow zone is preferably in the range from 7:1 to 3:1, particularly preferably in the range from 5:1 to 3:1 and very particularly preferably in the range from 4:1 to 3:1, for example 3:1.

The plug-flow zone is preferably configured such that the flow through it is turbulent. Turbulent flow is presently to be understood as meaning a Reynolds number Re of more than 3000. Thus:

$$\mathrm{Re} = \frac{\rho v d}{\eta} > 2000$$

wherein $\rho$ represents the density of the reaction mixture, $v$ represents the flow rate of the reaction mixture, $d$ represents the characteristic length of the plug-flow zone and $\eta$ represents the dynamic viscosity of the reaction mixture. The characteristic length of the plug-flow zone is the hydraulic diameter, namely 2×the gap width.

It follows from the above that turbulence increases the smaller the annular thickness. For construction-related reasons the annular thickness is preferably at least 2 cm.

The pressure difference between the backmixed zone, the zone of limited backmixing and the plug-flow zone corresponds only to the pressure drop resulting from traversal of the backmixing-preventing third internal elements of the zone of limited backmixing. Advantageously, the first, second and third internal elements may therefore be configured independently of the pressure intended for the process to be performed.

The invention further relates to a process for performing a continuous reaction, wherein
  a first fluid of higher density and a second fluid of lower density are introduced into the backmixed zone of a reactor according to any of the preceding claims so that at least the first fluid consecutively traverses the backmixed zone, the zone of limited backmixing and the plug-flow zone and
  the first fluid comprising a reaction product is withdrawn at the reaction product outlet of the plug-flow zone.

The process is preferably carried out such that unconverted second fluid is at least partially discharged from the backmixed zone via an outlet. It is particularly preferable when the first fluid is a liquid and the second fluid is a gas.

The gas is preferably dispersed in the liquid in the backmixed zone, wherein the liquid consecutively traverses the zone of limited backmixing and the plug-flow zone, wherein the volume ratio of dispersed gas to the liquid decreases in the flow direction from the zone of limited backmixing to the plug-flow zone so that the plug-flow zone is traversed by the substantially single-phase liquid.

In one embodiment the process is a process for performing a high-pressure reaction. A high-pressure reaction is to be understood as meaning a reaction performed at a pressure elevated with respect to ambient pressure, for example at at least 5 bar absolute, at least 20 bar absolute or at least 50 bar absolute.

It is preferable when the volume ratio of gas dispersed in the reaction mixture to liquid decreases in the direction of traversal of the zone of limited backmixing so that a substantially monophasic liquid emerges from the zone of limited backmixing.

In a preferred embodiment the gas is hydrogen. Particular preference is given to a process for producing an optically active carbonyl compound by asymmetric hydrogenation of a prochiral α,β-unsaturated carbonyl compound with hydrogen in the presence of a homogeneous rhodium catalyst comprising at least one chiral ligand.

A prochiral α,β-unsaturated carbonyl compound can form a chirality center through an addition reaction at the olefinic double bond. To this end the double bond bears four different substituents. The prochiral α,β-unsaturated carbonyl compound is preferably selected from compounds of general formula (I)

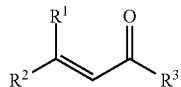
(I)

wherein $R^1$, $R^2$ are distinct from one another and each represent an unbranched, branched or cyclic hydrocarbon radical having 1 to 25 carbon atoms which is saturated or comprises one or more, nonconjugated ethylenic double bonds and which is unsubstituted or bears one or more identical or different substituents selected from $OR^4$, $NR^{5a}R^{5b}$, halogen, $C_6$-$C_{10}$-aryl and hetaryl having 5 to 10 ring atoms, $R^3$ represents hydrogen or an unbranched, branched or cyclic hydrocarbon radical having 1 to 25 carbon atoms which is saturated or comprises one or more, nonconjugated ethylenic double bonds and which is unsubstituted or bears one or more identical or different substituents selected from $OR^4$, $NR^{5a}R^{5b}$, halogen, $C_6$-$C_{10}$-aryl and hetaryl having 5 to 10 ring atoms, or $R^3$ jointly with either of the radicals $R^1$ or $R^2$ may also represent a 3- to 25-membered alkylene group wherein 1, 2, 3 or 4 nonadjacent $CH_2$-groups may be replaced by O or N—$R^{5c}$, wherein the alkylene group is saturated or comprises one or more nonconjugated ethylenic double bonds and wherein the alkylene group is unsubstituted or bears one or more identical or different substituents selected from $OR^4$, $NR^{5a}R^{5b}$, halogen, $C_1$-$C_4$-alkyl, $C_6$-$C_{10}$-aryl and hetaryl having 5 to 10 ring atoms, wherein two substituents may also jointly represent a 2- to 10-membered alkylene group, wherein the 2- to 10-membered alkylene group is saturated or comprises one or more nonconjugated ethylenic double bonds and wherein the 2- to 10-membered alkylene group is unsubstituted or bears one or more identical or different substituents selected from $OR^4$, $NR^{5a}R^{5b}$, halogen, $C_6$-$C_{10}$-aryl and hetaryl having 5 to 10 ring atoms;

wherein $R^4$ represents hydrogen, $C_1$-$C_6$-alkyl, $C_6$-$C_{10}$-aryl, $C_6$-$C_{14}$-aryl-$C_1$-$C_{10}$-alkyl, or $C_1$-$C_{10}$-alkyl-$C_6$-$C_{14}$-aryl;

$R^{5a}$, $R^{5b}$ each independently of one another represent hydrogen, $C_1$-$C_6$-alkyl, $C_6$-$C_{10}$-aryl, $C_6$-$C_{14}$-aryl-$C_1$-$C_{10}$-alkyl or $C_1$-$C_{10}$-alkyl-$C_6$-$C_{14}$-aryl or $R^{5a}$ and $R^{5b}$ may also jointly represent an alkylene chain having 2 to 5 carbon atoms which may be interrupted by N or O; and $R^{5c}$ represents hydrogen, $C_1$-$C_6$-alkyl, $C_6$-$C_{10}$-aryl, $C_6$-$C_{14}$-aryl-$C_1$-$C_{10}$-alkyl, or $C_1$-$C_{10}$-alkyl-$C_6$-$C_{14}$-aryl.

In preferred embodiments the prochiral α,β-unsaturated carbonyl compound is selected from compounds of general formulae (Ia) and (Ib)

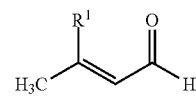
(Ia)

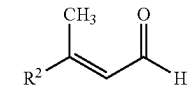
(Ib)

wherein $R^1$, $R^2$ each represent an unbranched or branched hydrocarbon radical having 2 to 25 carbon atoms which is saturated or comprises 1, 2, 3, 4 or 5 nonconjugated ethylenic double bonds.

A particularly preferred embodiment relates to a process for producing optically active citronellal of formula (III)

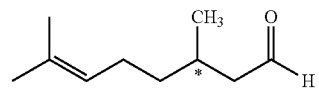
(III)

wherein * denotes the asymmetric center;

by asymmetric hydrogenation of geranial of formula (Ia-1) or of neral of formula (Ib-1)

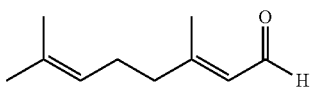
(Ia-1)

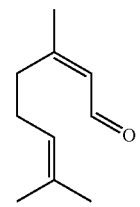
(Ib-1)

or of a mixture comprising neral and geranial. A mixture comprising neral and geranial is known as citral.

The thus obtainable optically active citronellal of formula (III) may be subjected to a cyclization to afford optically active isopulegol and the optically active isopulegol hydrogenated to afford optically active menthol.

This process for producing an optically active carbonyl compound makes it possible to provide optically active carbonyl compounds, in particular optically active aldehydes in high yields and enantiomeric excesses. The desired asymmetrically hydrogenated compounds are typically obtained in an enantiomeric excess of at least 80% ee, often with an enantiomeric excess of about 85% to about 99% ee. It should be noted that the maximum achievable enantiomeric excess may depend on the purity of the employed substrate, especially in respect of the isomeric purity of the double bond to be hydrogenated. Particularly suitable starting substances are accordingly those having an isomer ratio of at least about 90:10, preferably at least about 95:5, in respect of the E/Z double bond isomers.

This preferred process for producing an optically active carbonyl compound is performed in the presence of an optically active rhodium catalyst soluble in the reaction mixture and comprising at least one optically active ligand. Such catalysts are obtainable for example by reaction of a suitable rhodium compound soluble in the reaction mixture with an optically active ligand comprising at least one phosphorus and/or arsenic atom.

Examples of rhodium compounds employable according to the invention include: RhCl$_3$, Rh(OAc)$_3$, [Rh(cod)Cl]$_2$, Rh(CO)$_2$acac, [Rh(cod)OH]$_2$, [Rh(cod)OMe]$_2$, Rh$_4$(CO)$_{12}$, Rh$_6$(CO)$_{16}$, wherein "acac" stands for an acetylacetonate ligand and "cod" stands for a cyclooctadiene ligand.

The catalyst concentration in the reaction mixture is preferably 0.001 to 1 mol %, in particular 0.002 to 0.5 mol %, particularly preferably 0.005 to 0.2 mol %, based on the amount of prochiral α,β-unsaturated carbonyl compound in the reaction mixture calculated as rhodium atoms present in the catalyst.

The recited rhodium compounds are contacted with a further compound which is optically active, preferably substantially enantiomerically pure (i.e. having an enantiomeric excess of at least about 99%), and comprises at least one phosphorus and/or arsenic atom, preferably at least one phosphorus atom. This compound to be described as the chiral ligand forms the rhodium catalyst to be employed according to the invention with the employed rhodium compound in the reaction mixture/in the preforming mixture.

Such chiral ligands which comprise two phosphorus atoms and form chelate complexes with rhodium are especially preferred.

Chiral ligands suitable in the context of the present invention include compounds such as are described for example in: I. Ojima (ed.), Catalytic Asymmetric Synthesis, Wiley-VCh, 2nd edition, 2000 or in E. N. Jacobsen, A. Pfaltz, H. Yamamoto (ed.), Comprehensive Asymmetric Catalysis, 2000, Springer or in W. Tang, X. Zhang, Chem. Rev. 2003, 103, 3029-3069.

Preferred ligands are chiral bidentate bisphosphine ligands, particularly those of general formulae (IV) to (VI)

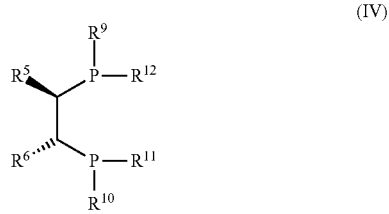

(IV)

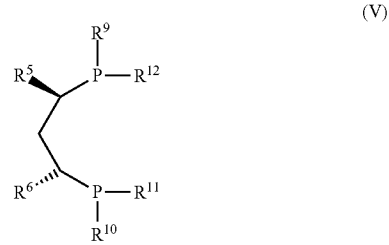

(V)

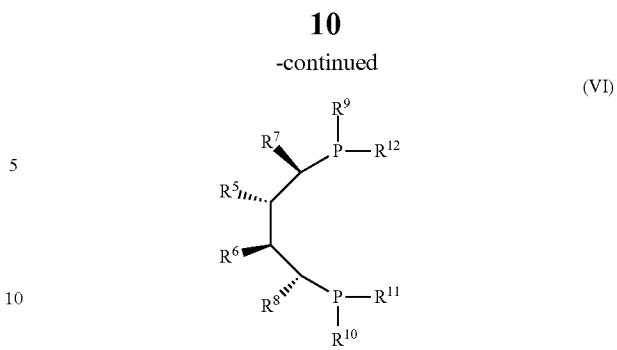

(VI)

wherein
R$^5$, R$^6$ each independently of one another represent an unbranched, branched or cyclic hydrocarbon radical having 1 to 20 carbon atoms which is saturated or may comprise one or more, generally 1 to about 4, nonconjugated ethylenic double bonds and which is unsubstituted or bears one or more, generally 1 to 4, identical or different substituents selected from OR$^{13}$, NR$^{14}$R$^{15}$, halogen, C$_6$-C$_{10}$-aryl and C$_3$-C$_9$-hetaryl, or R$^5$ and R$^6$ may jointly represent a 2- to 10-membered alkylene group or a 3- to 10-membered cycloalkylene group, wherein 1, 2, 3 or 4 nonadjacent CH groups may be replaced by O or N—R$^{13}$, wherein the alkylene group and the cycloalkylene group are saturated or comprise one or two nonconjugated ethylenic double bonds and wherein the alkylene group and the cycloalkylene group are unsubstituted or bear one or more identical or different substituents selected from C$_1$-C$_4$-alkyl;

R$^7$, R$^8$ each independently of one another represent hydrogen or straight-chain or branched C$_1$-C$_4$-alkyl and R$^9$, R$^{10}$, R$^{11}$, R$^{12}$ are identical or different and represent C$_6$-C$_{10}$-aryl which is unsubstituted or bears one or more substituents selected from C$_1$-C$_6$-alkyl, C$_3$-C$_6$-cycloalkyl, C$_6$-C$_{10}$-aryl, C$_1$-C$_6$-alkoxy and amino;

R$^{13}$, R$^{14}$, R$^{15}$ each independently of one another represent hydrogen, C$_1$-C$_4$-alkyl, C$_6$-C$_{10}$-aryl, C$_7$-C$_{12}$-aralkyl or C$_7$-C$_{12}$-alkylaryl, wherein R$^{14}$ and R$^{15}$ may also jointly represent an alkylene chain having 2 to 5 carbon atoms which may be interrupted by N or O.

Having regard to the formulae (IV), (V), and (VI) the variables are especially as follows:

R$^5$, R$^6$ each independently of one another represent C$_1$-C$_4$-alkyl or

R$^5$ and R$^6$ jointly represent a C$_3$-C$_5$-alkanediyl radical, C$_3$-C$_7$-alkenediyl radical, C$_5$-C$_7$-cycloalkanediyl radical or a C$_5$-C$_7$-cycloalkenediyl radical, wherein the four above-mentioned radicals are unsubstituted or bear one or more identical or different substituents selected from C$_1$-C$_4$-alkyl;

R$^7$, R$^8$ each independently of one another represent hydrogen or C$_1$-C$_4$-alkyl;

R$^9$, R$^{10}$, R$^{11}$, R$^{12}$ each represent phenyl.

Chiral, bidentate bisphosphine ligands particularly preferred on account of being readily available are compounds obtainable under the designation "chiraphos" and having the formula:

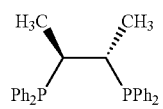

The chiral ligands are advantageously employed in an amount of about 0.9 to about 10 mol, preferably about 1 to about 4 mol, per mol of employed rhodium compound. The optically active rhodium catalyst soluble in the reaction mixture is suitably generated in situ by reacting an achiral rhodium compound with a chiral, bidentate bisphosphine ligand before or during the hydrogenation. In the present context the term "in situ" is to be understood as meaning that the catalyst is generated immediately before or at commencement of the hydrogenation. The catalyst is preferably generated before the hydrogenation.

It has been found that the presence of monodentate ligands can increase the activity of the catalyst. A preferred embodiment of the process according to the invention employs compounds of formula (II)

(II)

wherein Z in formula (II) represents a $CHR^{18}R^{19}$ group and wherein the variables $R^{16}$, $R^{17}$, $R^{18}$, $R^{19}$ independently of one another and especially jointly are as follows:

$R^{16}$, $R^{17}$: are identical or different and represent phenyl which is unsubstituted or bears 1, 2 or 3 substituents selected from methyl and methoxy, wherein $R^{16}$ and $R^{17}$ each especially represent unsubstituted phenyl;

$R^{18}$ represents $C_1$- to $C_4$-alkyl, especially methyl;

$R^{19}$ represents $C_1$- to $C_4$-alkyl bearing a $P(=O)R^{19a}R^{19b}$ group and especially a $CH_2$—$P(=O)R^{19a}R^{19b}$ or $CH(CH_3)$—$P(=O)R^{19a}R^{19b}$ group;

wherein $R^{19a}$, $R^{19b}$: are identical or different and represent phenyl which is unsubstituted or bears 1, 2 or 3 substituents selected from methyl and methoxy, wherein particularly preferably $R^{19a}$ and $R^{19b}$ each represent unsubstituted phenyl.

In this preferred embodiment of the process according to the invention it is particularly preferable to employ a compound of formula (II), wherein $R^{16}$, $R^{17}$: represent unsubstituted phenyl;

$R^{18}$ represents methyl;

$R^{19}$ represents a $CH(CH_3)$—$P(=O)R^{19a}R^{19b}$ group, wherein $R^{19a}$ and $R^{19b}$ each represent unsubstituted phenyl.

This is the compound (2-(diphenylphosphoryl)-1-methylpropyl)diphenylphosphane (chiraphos monooxide) including the (R,R) enantiomer (=(R,R)-chiraphos monooxide) and the (S,S) enantiomer (=(S,S)-chiraphos monooxide) and mixtures of (R,R)-chiraphos monooxide and (S,S)-chiraphos monooxide.

When the radicals $R^{18}$ and $R^{19}$ in general formula (II) are different the carbon atom bearing the radicals $R^{18}$ and $R^{19}$ may have an (R) or (S) configuration. These compounds of general formula (II) may be in the form of pure (R) or pure (S) stereoisomers or mixtures thereof. Generally employed in these cases are the pure (R) and (S) stereoisomers, wherein any stereoisomer mixtures are also suitable for use in the present process.

A pure stereoisomer is here and hereinbelow to be understood as meaning chiral substances which in terms of the desired stereoisomer have an enantiomeric excess (ee) of at least 80% ee, in particular at least 90% ee and especially 95% ee.

In particular, the chiral ligand employed is chiraphos and the monodentate compound employed is (2-(diphenylphos-phoryl)-1-methylpropyl)diphenylphosphane (chiraphos monooxide). By way of example the chiral ligand employed is R-chiraphos and the monodentate compound employed is (R,R)-chiraphos monooxide and/or (S,S)-chiraphos monooxide. Alternatively the chiral ligand employed is S-chiraphos and the monodentate compound employed is (R,R)-chiraphos monooxide and/or (S,S)-chiraphos monooxide.

According to the invention the compound of formula (II) is generally employed in an amount of 0.01 to 1 mol, preferably 0.02 to 0.8 mol, particularly preferably 0.03 to 0.7 mol and especially in an amount of 0.04 to 0.6 mol per mol.

Further embodiments of the hydrogenation catalyst and of the monodentate ligand are described in US 2018/0057437 A1, WO 2006/040096 A1 and WO 2008/132057 A1.

In one embodiment two mutually immiscible liquids of different density are introduced into the reactor and form a biphasic reaction mixture. For example the first fluid is a water-immiscible organic liquid and the second fluid an aqueous liquid.

In one embodiment the process is a process for producing a β-hydroxy ketone, wherein the first fluid comprises a dialkyl ketone and the second fluid comprises a formaldehyde source.

The dialkyl ketone is preferably selected from dimethyl ketone, diethyl ketone and dipropyl ketone and is especially diethyl ketone. The formaldehyde source provides formaldehyde in the liquid phase or as a gas phase. The formaldehyde source is preferably an aqueous formaldehyde solution. For example the aqueous formaldehyde solution comprises at least 15% by weight, especially at least 25% by weight or at least 35% by weight or at least 45% by weight of formaldehyde.

Preferably produced in this way is 1-hydroxy-2-methyl-3-pentanone (HMP), wherein the first fluid comprises diethyl ketone and the second fluid comprises an aqueous formaldehyde solution.

Also contemplated are hydrolysis reactions, wherein the first fluid comprises a water-immiscible liquid and the second fluid comprises aqueous sodium hydroxide solution.

The invention is more particularly elucidated by the accompanying FIGURE.

FIG. 1 is a schematic diagram of a reactor according to the invention for performing a process according to the invention.

According to FIG. 1 a reactor according to the invention is divided by internals into a backmixed zone 101, a zone of limited backmixing 102 and a plug-flow zone 103. The reactor comprises a stirrer 104. A first fluid of higher density, for example a liquid, is supplied to the reactor via conduit 105. A second fluid of lower density, for example a gas, is supplied to the reactor via conduit 106. The reactor is configured such that the reaction mixture consecutively traverses the backmixed zone 101, the zone of limited backmixing 102 and the plug-flow zone 103. Any offgas generated during the reaction is discharged from the reactor at a fluid outlet via conduit 107. The reaction product is withdrawn via conduit 108 at a reaction product outlet.

The invention claimed is:

1. A reactor for performing a reaction between two immiscible fluids of different density, comprising:
 an interior formed by a cylindrical, vertically oriented elongate shell, a bottom and a cap,
 wherein the interior is divided by internals into a backmixed zone, a zone of limited backmixing arranged below the backmixed zone and a plug-flow zone which are at least consecutively traversable by one of the fluids, wherein the backmixed zone comprises at least one inlet and the plug-flow zone comprises an outlet and the backmixed zone comprises at least one mixing apparatus selected from a stirrer, a jet nozzle and means for injecting the fluid of lower density;

a first cylindrical internal element which in the interior extends in the longitudinal direction of the reactor, which delimits the zone of limited backmixing from the plug-flow zone and which comprises a first passage to the backmixed zone and a second passage to the plug-flow zone, wherein the first internal element is arranged concentrically to the shell so that the plug-flow zone has an annular horizontal cross section, and wherein the lower edge of the first internal element is arranged at a distance from the bottom of the reactor, a second internal element which delimits the backmixed zone from the plug-flow zone such that there is no direct fluid connection between the backmixed zone and the plug-flow zone, wherein the second internal element extends from the upper edge of the first internal element to the shell, and wherein the second internal element is a horizontally oriented annular plate, and backmixing-preventing third internal elements in the form of random packings, structured packings or liquid-permeable trays arranged in the zone of limited backmixing.

2. The reactor according to claim 1, wherein the plug-flow zone is arranged such that the flow through it is turbulent.

3. The reactor according to claim 1, wherein the second internal element divides the interior in the vertical direction into an upper half and a lower half in the ratio of 4:1 to 1:1.

4. The reactor according to claim 1, wherein the mixing apparatus is a jet nozzle.

5. A process for performing a continuous reaction, wherein
a first fluid of higher density and a second fluid of lower density are introduced into the backmixed zone of the reactor according to claim 1 so that at least the first fluid consecutively traverses the backmixed zone, the zone of limited backmixing and the plug-flow zone, and
the first fluid comprising a reaction product is withdrawn at the reaction product outlet of the plug-flow zone.

6. The process according to claim 5, wherein unconverted second fluid is at least partially discharged from the backmixed zone via an outlet.

7. The process according to claim 5, wherein the first fluid is a liquid and the second fluid is a gas.

8. The process according to claim 7 for performing a high-pressure reaction.

9. The process according to claim 7, wherein the gas is dispersed in the liquid in the backmixed zone, the liquid consecutively traverses the zone of limited backmixing and the plug-flow zone, wherein the volume ratio of dispersed gas to the liquid decreases in the flow direction from the zone of limited backmixing to the plug-flow zone so that the plug-flow zone is traversed by the substantially single-phase liquid.

10. The process according to claim 7 for producing an optically active carbonyl compound by asymmetric hydrogenation of a prochiral α,β-unsaturated carbonyl compound with hydrogen in the presence of a homogeneous rhodium catalyst comprising at least one chiral ligand.

11. The process according to claim 10, wherein the process is performed in the presence of a compound of formula (II)

wherein Z in formula (II) represents a CHR$^3$R$^4$ group and wherein the variables R$^1$, R$^2$, R$^3$, R$^4$ independently of one another and especially jointly are as follows:
R$^1$, R$^2$: are identical or different and represent phenyl which is unsubstituted or bears 1, 2 or 3 substituents selected from methyl and methoxy;
R$^3$ represents C$_1$- to C$_4$-alkyl;
R$^4$ represents C$_1$- to C$_4$-alkyl bearing a P(=O)R$^{4a}$R$^{4b}$ group;
wherein
R$^{4a}$, R$^{4b}$: are identical or different and represent phenyl which is unsubstituted or bears 1, 2 or 3 substituents selected from methyl and methoxy.

12. A process for producing optically active menthol in which optically active citronellal of formula (III)

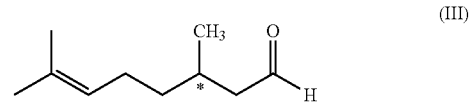

wherein * denotes the asymmetric center;
is produced by the process according to claim 10 by asymmetric hydrogenation of geranial of formula (Ia-1) or of neral of formula (Ib-1)

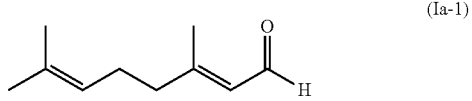

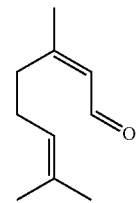

or of a mixture comprising neral and geranial,
the optically active citronellal of formula (III) is subjected to a cyclization to afford optically active isopulegol and the optically active isopulegol is hydrogenated to afford optically active menthol.

13. The process according to claim 5, wherein the first fluid is a water-immiscible organic liquid and the second fluid is an aqueous liquid.

14. The process according to claim 13 for producing a β-hydroxy ketone, wherein the first fluid comprises a dialkyl ketone and the second fluid comprises a formaldehyde source.

15. The process according to claim 10, wherein the at least one chiral ligand is chiraphos.

16. The process according to claim 11, wherein $R^1$ and $R^2$ each represent unsubstituted phenyl.

17. The process according to claim 11, wherein $R^3$ represents methyl.

18. The process according to claim 11, wherein $R^4$ represents a $CH_2$—$P(=O)R^{4a}R^{4b}$ or $CH(CH_3)$—$P(=O)R^{4a}R^{4b}$ group.

19. The process according to claim 11, wherein $R^{4a}$ and $R^{4b}$ each represent unsubstituted phenyl.

20. The process according to claim 16, wherein $R^3$ represents methyl, $R^4$ represents a $CH_2$—$P(=O)R^{4a}R^{4b}$ or $CH(CH_3)$—$P(=O)R^{4a}R^{4b}$ group and $R^{4a}$ and $R^{4b}$ each represent unsubstituted phenyl.

* * * * *